US009796665B2

(12) United States Patent
Jeong et al.

(10) Patent No.: US 9,796,665 B2
(45) Date of Patent: Oct. 24, 2017

(54) CERAMIDE DERIVATIVES HAVING AGONISTIC EFFECTS ON EPIDERMAL CANNABINOID RECEPTORS, AND PHARMACEUTICAL OR COSMETIC COMPOSITION CONTAINING SAME

(71) Applicant: NEOPHARM CO., LTD., Yuseong-gu, Daejeon (KR)

(72) Inventors: Se Kyoo Jeong, Daejeon (KR); Bong-Woo Kim, Daejeon (KR); Jeong Eun Jeon, Daejeon (KR); Bu-Mahn Park, Daejeon (KR)

(73) Assignee: NEOPHARM CO., LTD., Daejeon (KR)

( * ) Notice: Subject to any disclaimer, the term of this patent is extended or adjusted under 35 U.S.C. 154(b) by 0 days.

(21) Appl. No.: 14/916,079

(22) PCT Filed: Sep. 1, 2014

(86) PCT No.: PCT/KR2014/008149
§ 371 (c)(1),
(2) Date: Mar. 2, 2016

(87) PCT Pub. No.: WO2015/034228
PCT Pub. Date: Mar. 12, 2015

(65) Prior Publication Data
US 2016/0272578 A1     Sep. 22, 2016

(30) Foreign Application Priority Data
Sep. 3, 2013  (KR) .................. 10-2013-0105741

(51) Int. Cl.
*C07C 235/76*     (2006.01)
*C07C 233/80*     (2006.01)

(52) U.S. Cl.
CPC .......... *C07C 235/76* (2013.01); *C07C 233/80* (2013.01)

(58) Field of Classification Search
CPC ........................... C07C 235/76; C07C 233/80
USPC ........................................................ 514/627
See application file for complete search history.

(56) References Cited

U.S. PATENT DOCUMENTS

| 7,344,868 | B2 | 3/2008 | Lassalle et al. |
| 2010/0286102 | A1 | 11/2010 | Vielhaber |
| 2011/0306672 | A1 | 12/2011 | Brinkmann et al. |

FOREIGN PATENT DOCUMENTS

| KR | 10-2010-0001374 A | 1/2010 |
| KR | 10-1051812 B1 | 7/2011 |
| KR | 10-2013-0030093 A | 3/2013 |

OTHER PUBLICATIONS

Y. Gaoni et al., "Isolation, Structure, and Partial Synthesis of an Active Constituent of Hashish," Communications to the Editor, vol. 86(8) 1964, pp. 1646-1647, 2 pages total.
Roger G. Pertwee, "Pharmacology of Cannabinoid $CB_1$ and $CB_2$ Receptors". Pharmacol. Ther. vol. 74, No. 2, pp. 129-180, 1997.
A. C. Howlett et al., "International Union of Pharmacology. XXVII. Classification of Cannabinoid Receptors", Pharmacological Reviews 54: pp. 161-202, 2002.
Thomas W. Klein et al., "Cannabinoid receptors and immunity", Immunology Today, 1998, 19(8), pp. 373-381, 9 pages total.
Stephen I. Wasserman, M.D., "Mediators of immediate hypersensitivity", The Journal of Allergy and Clinical Immunology, Continuing Medical Education, vol. 72, No. 2, 1983, pp. 101-115.
Kelly D. Stone, MD et al., "IgE, mast cells, basophils, and eosinophils", J Allergy Clin. Immunol., vol. 125, No. 2, Feb. 2010, pp. S73-S80, 8 pages total.
Luigi Aloe et al., "A proposed autacoid mechanism controlling mastocyte behaviour", Agents Actions, 39, Special Conference Issue (1993), pp. C145-C147, 3 pages total.
L. Facci et al., "Mast cells express a peripheral cannabinoid receptor with differential sensitivity to anandamide and palmitoylethanolamide", Proc. Natl. Acad. Sci., vol. 92, pp. 3376-3380, Apr. 1995, 5 pages total.
Kent-Olov Jonsson et al., "The cannabinoid $CB_2$ receptor selective agonist JWH133 reduces mast cell oedema in response to compound 48/80 in vivo but not the release of beta-hexosaminidase from skin slices in vitro", Life Sciences 78 (2006), pp. 598-606.
Elda Del Giudice et al., "Cannabidiol, unlike synthetic cannabinoids, triggers activation of RBL-2H3 mast cells", Journal of Leukocyte Biology, vol. 81, Jun. 2007, pp. 1512-1522.
Marie-Anne Morren et al., "Atopic dermatitis: Triggering factors", Journal of the American Academy of Dermatology, vol. 31, No. 3, Part 1, Sep. 1994, pp. 467-473.
M. Jutel et al., "Histamine, histamine receptors and their role in immune pathology", Clinical & Experimental Allergy, 39, pp. 1786-1800, 2009.
Guillermo Velasco, et al., "Cannabinoids and ceramide: Two lipids acting hand-by-hand", Life Sciences, 2005, pp. 1723-1731, vol. 77.
International Searching Authority, International Search Report for PCT/KR2014/008149 dated Nov. 24, 2014 [PCT/ISA/210].
International Searching Authority, Written Opinion for PCT/KR2014/008149 dated Nov. 24, 2014 [PCT/ISA/237].

*Primary Examiner* — Sabiha N Qazi
(74) *Attorney, Agent, or Firm* — Sughrue Mion, PLLC

(57) ABSTRACT

The present invention relates to a novel pseudoceramide derivative, a pharmaceutically acceptable salt thereof or a solvate thereof, and a pharmaceutical or cosmetic composition containing the same as an active ingredient. The novel pseudoceramide derivative of the present invention is expected to be very useful for treating or preventing skin diseases by activating cannabinoid receptors. In addition, the novel pseudoceramide derivative, the pharmaceutically acceptable salt thereof or the solvate thereof, of the present invention, has a simple synthesis process compared with a known cannabinoid receptor antagonist so as to reduce processing time and curtail material costs, and thus is economical, and has advantages such as easy emulsification during the formulation of cosmetic products or medical supplies.

10 Claims, 8 Drawing Sheets

(A) (B)

(A)

(B)

(A)

(B)

CERAMIDE DERIVATIVES HAVING AGONISTIC EFFECTS ON EPIDERMAL CANNABINOID RECEPTORS, AND PHARMACEUTICAL OR COSMETIC COMPOSITION CONTAINING SAME

CROSS REFERENCE TO RELATED APPLICATION

This application is a National Stage of International Application No. PCT/KR2014/008149 filed Sep. 1, 2014, claiming priority based on Korean Patent Application No. 10-2013-0105741 filed Sep. 3, 2013, the contents of all of which are incorporated herein by reference in their entirety.

TECHNICAL FIELD

The present invention relates to a novel ceramide derivative, and more particularly, to a novel ceramide derivative for treating or preventing a skin disease as an agonist of epidermal cannabinoid receptor 1, and a pharmaceutical composition containing a pharmaceutically acceptable salt or solvate thereof.

In addition, the present invention relates to a novel ceramide derivative, and a cosmetic composition for alleviating a skin disease, containing a pharmaceutically acceptable salt or solvate thereof as an active ingredient.

BACKGROUND ART

Cannabinoids are present in *Cannbis sativa* containing 100 kinds or more of $C_{21}$ terpenophenol based compounds [Y. Gaoni R M., J. AM. Chem. Soc. 1964, 86(8): 1646-1647]. 9-thetrahydrocannabinol (THC), which is the best-known among them, binds to a cannabinoid receptor known as a G-protein-coupled receptor (GPCR) in a human body to cause a mental effect [Pertwee R G., Pharmacol. Ther. 1997, 74(2): 129-180]. After two different subtypes (CB1R and CB2R) of the cannabinoid receptors were found and cloned, research into a novel cannabinoid receptor antagonist has been promoted, such that various kinds of cannabinoid receptor antagonists have been developed. In addition, it was found that anandamide (AEA), 2-arachidonyl glycerol (2-AG), palmitoylethanolamide (PEA), and the like, which are endogenous cannabinoids binding to the cannabinoid receptor to act thereon, were present in the body [Pertwee R G., Pharmacol. Ther. 1997, 74, 129-180].

The cannabinoid receptor 1 (CB1R) was mainly expressed in a central nervous system, but recently, it was confirmed that the cannabinoid receptor 1 (CB1R) was also expressed in a peripheral nervous system and immune cells, and the cannabinoid receptor 2 (CB2R) was mainly expressed in an immune system such as B cells, T cells, macrophages, lymph nodes [Howlett A C, Barth F, Bonner T I, Cabral G, Casellas P, Devane W A, et al., *Pharmacological Reviews* 2002, 54(2): 161-202]. Particularly, it was found that both of the CB1R and CB2R were expressed in mast cells, a kind of immune cells, and the cannabinoid receptor antagonists may regulate an activity of the mast cells [Klein T W, Newton C, Friedman H., *Immunology Today* 1998, 19(8): 373-381].

It was known that activation of the mast cells was important for various allergy responses and inflammatory responses [Wasserman S I., J. Allergy Clin. Immunol. 1983; 72: 101-119]. The mast cells playing an important role in an innate immunity system regulate inflammatory responses and repair and remodeling of damaged tissue in addition to serving as a defense mechanism against infection [Stone K D, Prussin C, Metacalfe D D., J. Allergy Clin. Immunol. 2010, 125: S73-80]. The mast cells were immunologically activated by receptor cross-linking by immunoglobulin E (IgE) binding to high affinity IgE receptors, but a physiological regulation mechanism on cytokine release of the mast cells was not known yet. Recently, it was reported that endogenous cannabinoids may serve as autacoids inhibiting activation of mast cells and suppressing local inflammatory responses [Aloe L, Leon A, Levi-Montalcini R., Agents Actions 1993, 39: C145-C147]. Facci et al, initially reported in 1995 that CB2R, which is the cannabinoid receptor, was expressed in mast cells present in the peritoneum of a rat and RBL-2H3, which is a rat basophilic leukaemia cell line, and they confirmed that release of cytokines was suppressed in the mast cells by PEA, thereby asserting that activation of the CB2R suppress inflammation [Facci L, Dal Toso R, Romanello S, Buriani A, Skaper S D, Leon A., Proc. Natl. Acad. Sci. USA. 1995, 92: 3376-3380]. It was reported that in rats to which PEA was orally administered, formation of oedema was decreased, inflammatory hyperalgesia was also decreased, and a synthesized cannabinoid JWH133, which is known as a CB2R agonist decreases oedema by mast cells [Kent-Olov J, Emma P, Christopher J F., Life Sciences 2006, 78:598-606]. Meanwhile, roles of the CB1R in the mast cells were not well-known unlike the CB2R, but recently, research into the CB1R has been conducted. WIN 55,212-2, which was known as a selective CB1R agonist, suppresses release of b-hexosaminidase in RBL-2H3 mast cells [Giudice E D, Rinaldi L, Passarotto M, Facchinetti F, D'Arrigo A, Guiotto A et al., J. Leukoc. Biol. 2007, 81:1 512-1521].

Among skin diseases, atopic dermatitis is a representative disease of which symptoms are aggregated by excessive activation of the mast cells. Atopic dermatitis is a chronic recurrent skin disease, and the accurate causes of atopic dermatitis were not known, but it has been estimated that pathogenesis of atopic dermatitis was complicatedly associated with genetic, environmental, and immunologic factors [Morren M A, Przybilla B, Bamelis M, Heykants B, Reynaers A, Degreef H., J. Am. Acad. Dermatol., 1994, 31, 467-473]. In patients with atopic dermatitis, the mast cells were activated in both an IgE-dependent response and an IgE-independent response, such that plasma membrane and cytoplasmic fine membrane are fused with each other, thereby causing degranulation. When various allergens bind to specific IgE of the mast cells or basophils, the allergen strongly binds to an IgE receptor FceRI on surfaces of the mast cells, such that proteoglycan, eicosanoid, protease, and TNF-a, IL-4, IL-6, IL-13, TGF-β, and the like, which are various chemotactic cytokines, as well as histamine are released [Jutel M, Akdis M, & Akdis C A., Clin. Exp. Allergy 2009, 39(12): 1786-1800]. Among them, histamine, which is a strong vasoactive mediator having the most diverse characteristics, expands the blood vessel to induce a larger number of immune cells so as to move to a lesion site.

A material capable of suppressing activities of the mast cells to decrease histamine released therefrom and decreasing vascular permeability may provide efficacy more suitable for treating and preventing atopic dermatitis than a general immunosuppressive material. A technology of preventing and alleviating atopic dermatitis and itching according to the related art is to administer anti-histamine or use steroids, but at the time of administration or application of these medicines, side effects such as the central nervous system disorder, digestive disorder, numbness state, or the like, occur. Therefore, the development of a novel material and agent which may overcome these side effects and do not have toxicity has been required.

DISCLOSURE

Technical Problem

An object of the present invention is to provide a novel ceramide derivative capable of activating a cannabinoid receptor, and a pharmaceutically acceptable salt or solvate thereof.

Another object of the present invention is to provide a pharmaceutical composition containing a novel ceramide derivative or the pharmaceutically acceptable salt or solvate thereof as an active ingredient to thereby be useful to treat or prevent a skin disease such as atopic dermatitis.

Another object of the present invention is to provide a cosmetic composition for alleviating a skin disease, containing the novel ceramide derivative or the pharmaceutically acceptable salt or solvate thereof as an active ingredient.

Technical Solution

In one general aspect, there are provided a novel ceramide derivative represented by the following Chemical Formula 1, and a pharmaceutically acceptable salt or solvate thereof.

[Chemical Formula 1]

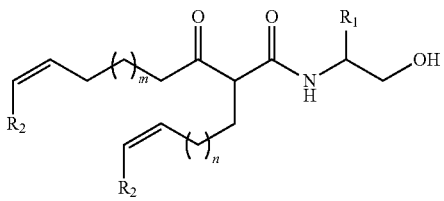

($R_1$ is hydrogen or hydroxy(C1-C10)alkyl, $R_2$ is (C1-C10) alkyl, and m and n are integers of 1 to 10.)

The ceramide derivative represented by Chemical Formula 1 may be selected from the following compounds.

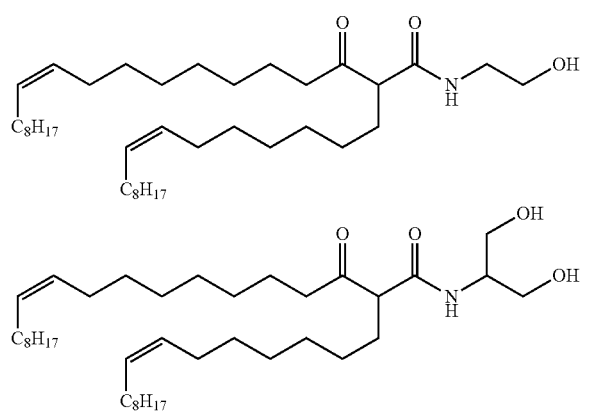

In another general aspect, there is provided a pharmaceutical composition for treating or preventing a skin disease, containing the pseudoceramide derivative represented by Chemical Formula 1, or the pharmaceutically acceptable salt or solvate thereof as an active ingredient.

The skin disease may be one or more selected from the group consisting of atopic dermatitis, allergic rhinitis, psoriasis, contact dermatitis, eczematous dermatitis, photodermatitis, seborrheic dermatitis, dermatitis herpetiformis, lichen planus, lichen sclerosus, pyoderma gangrenosum, pemphigus, epidermolysis bullosa, angioedema, blepharitis, allergic conjunctivitis, degenerative or inflammatory ophthalmitis, arthritis, rheumatoid arthritis, spondylitis, systemic sclerosis, dermatomyositis, polymyositis, inflammatory muscle diseases, acquired immune deficiency syndrome (AIDS), leprosy, Sezary syndrome, inflammatory bowel diseases, stress diseases, and transplant rejection.

In another general aspect, there is provided a cosmetic composition for alleviating a skin disease, containing the ceramide derivative represented by Chemical Formula 1, or the pharmaceutically acceptable salt or solvate thereof as an active ingredient.

The skin disease may be one or more selected from the group consisting of atopic dermatitis, allergic rhinitis, psoriasis, contact dermatitis, eczematous dermatitis, photodermatitis, seborrheic dermatitis, dermatitis herpetiformis, lichen planus, lichen sclerosus, pyoderma gangrenosum, pemphigus, epidermolysis bullosa, angioedema, blepharitis, allergic conjunctivitis, degenerative or inflammatory ophthalmitis, arthritis, rheumatoid arthritis, spondylitis, systemic sclerosis, dermatomyositis, polymyositis, inflammatory muscle diseases, acquired immune deficiency syndrome (AIDS), leprosy, Sezary syndrome, inflammatory bowel diseases, stress diseases, and transplant rejection.

Advantageous Effects

A novel ceramide derivative and a pharmaceutically acceptable salt or solvate thereof according to the present invention, which are excellent cannabinoid receptor antagonists, may be synthesized using a simple synthesis process as compared to a cannabinoid receptor antagonist according to the related art, and decrease a process time and a cost of a raw material, thereby having advantages of economical efficiency and ease of emulsification at the time of being formulated into a cosmetics or medicine.

In addition, the novel ceramide derivative and the pharmaceutically acceptable salt or solvate thereof according to the present invention may act as a cannabinoid receptor antagonist to suppress activities of mast cells, thereby being usefully used to treat and prevent a skin disease.

Further, a cosmetic composition according to the present invention may contain a novel pseudoceramide derivative, or a pharmaceutically acceptable salt or solvate thereof having an excellent antagonistic effect on a cannabinoid receptor as an active ingredient, thereby making it possible to prevent and treat a skin disease.

BEST MODE

Figure 1:
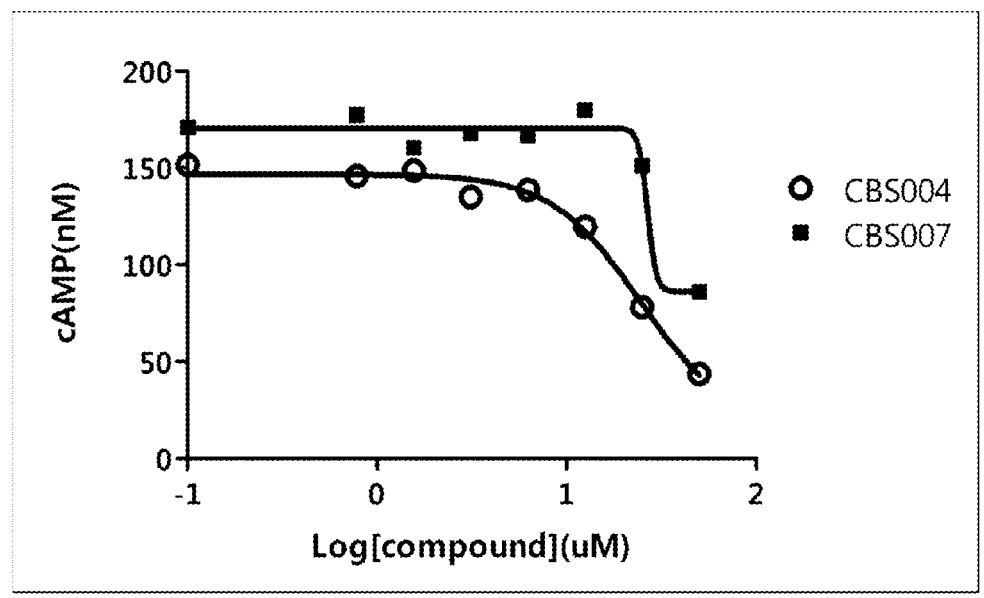
FIG. 1 is a graph illustrating agonistic activities of compounds CBS004 (Example 2) and CBS007 (Example 1) according to the present invention against a cannabinoid receptor, evaluated using a method according to Example 3, FIG. 2(A) and (B) are graphs illustrating suppression effects of the compounds CBS004 (Example 2) and CBS007 (Example 1) according to the present invention on activation of mast cells by ionomycin, evaluated using a method according to Example 4, FIG. 3(A) and (B) are graphs illustrating suppression effects of the compounds CBS004 (Example 2) and CBS007 (Example 1) according to the present invention on activation of the mast cells by IgE antibody and antigen, evaluated using a method in Example 5.

A novel ceramide derivative and a pharmaceutical or cosmetic composition containing the same according to the present invention will be described in detail below. Here, technical terms and scientific terms used in the present specification have the general meaning understood by those skilled in the art to which the present invention pertains unless otherwise defined, and a description for the known function and configuration unnecessarily obscuring the gist of the present invention will be omitted in the following description.

The present invention provides a novel ceramide derivative represented by the following Chemical Formula 1, and a pharmaceutically acceptable salt or solvate thereof.

[Chemical Formula 1]

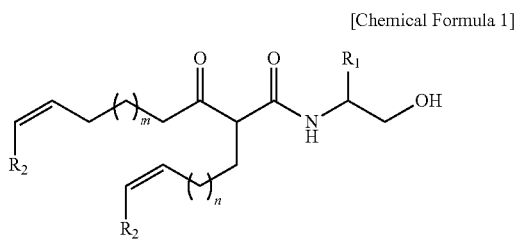

($R_1$ is hydrogen or hydroxy(C1-C10)alkyl, $R_2$ is (C1-C10) alkyl, and m and n are integers of 1 to 10.)

The novel ceramide derivative represented by Chemical Formula 1 and the pharmaceutically acceptable salt or solvate thereof according to the present invention may be selected from the following compounds, but are not limited thereto.

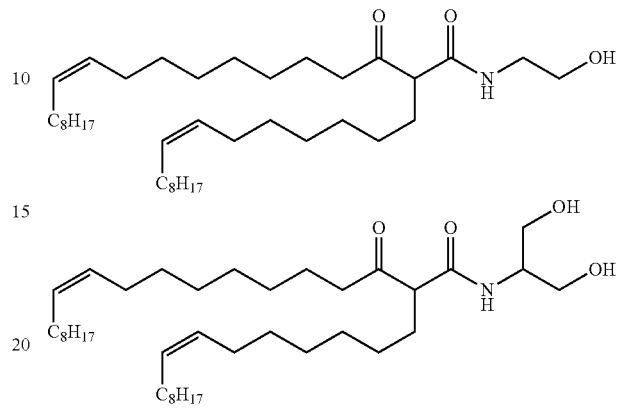

Synthesis of the ceramide derivative represented by Chemical Formula 1 and the pharmaceutically acceptable salt or solvate thereof is not particularly limited. For example, a general Synthesis Reaction Formula was illustrated below, and the ceramide derivative represented by Chemical Formula 1 and the pharmaceutically acceptable salt or solvate thereof may be prepared by an organic reaction known in the art.

[Reaction Formula]

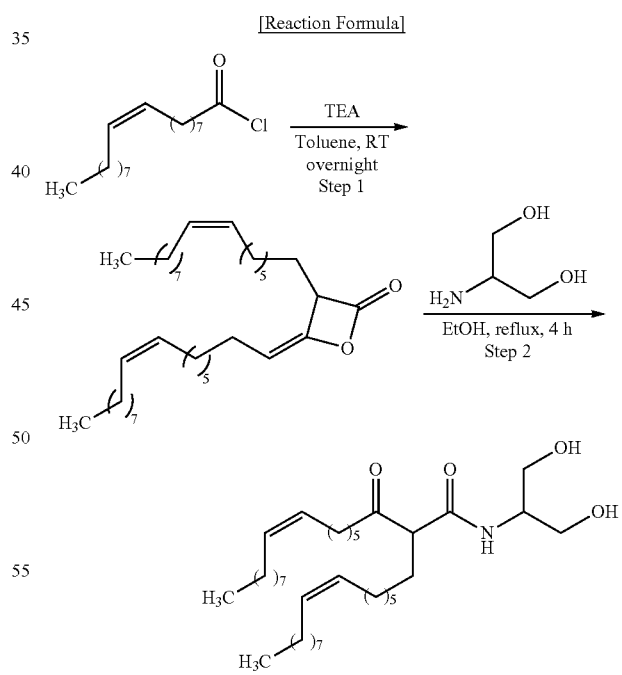

In addition, the present invention provides a pharmaceutical composition for treating or preventing a skin disease, containing a novel ceramide derivative represented by Chemical Formula 1, or a pharmaceutically acceptable salt or solvate thereof as an active ingredient.

In the pharmaceutical composition for treating or preventing a skin disease, the skin disease may be one or more selected from the group consisting of atopic dermatitis, allergic rhinitis, psoriasis, contact dermatitis, eczematous dermatitis, photodermatitis, seborrheic dermatitis, dermatitis herpetiformis, lichen planus, lichen sclerosus, pyoderma gangrenosum, pemphigus, epidermolysis bullosa, angioedema, blepharitis, allergic conjunctivitis, degenerative or inflammatory ophthalmitis, arthritis, rheumatoid arthritis, spondylitis, systemic sclerosis, dermatomyositis, polymyositis, inflammatory muscle diseases, acquired immune deficiency syndrome (AIDS), leprosy, Sezary syndrome, inflammatory bowel diseases, stress diseases, and transplant rejection.

A preferable dose of the pharmaceutical composition according to the present invention may be variously prescribed depending on factors such as a formulation method, an administration method, an age, a weight, sex, a disease state of a patient, foods, an administration time, an administration route, an excretion rate, and response sensitivity. For example, a daily dose of the pharmaceutical composition according to the present invention may be 0.001 to 100 mg/kg.

The pharmaceutical composition may be orally or parenterally administered, and in the case of parenteral administration, the pharmaceutical composition may be intravenously or subcutaneously injected, or transdermally administered, or the like.

The pharmaceutical composition according to the present invention may contain a pharmaceutically acceptable carrier. The pharmaceutically acceptable carrier contained in the pharmaceutical composition according to the present invention, which is generally used at the time of preparation, includes lactose, dextrose, sucrose, sorbitol, mannitol, starches, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, and the like, but is not limited thereto. The pharmaceutical composition according to the present invention may additionally include a lubricant, a wetting agent, a sweetener, a flavoring agent, an emulsifier, a suspending agent, a preservative, or the like, in addition to the above components.

The pharmaceutical composition according to the present invention may be prepared in a unit dose form or prepared in a form in which the pharmaceutical composition is input into a multi-dose container by being formulated into a general formulation using the pharmaceutically acceptable carrier and/or the excipient according to a method capable of being easily performed by those skilled in the art to which the present invention pertains. The general formation means, for example, oral formulations (tablets, capsules, powders) and formulations for sublingual, rectal, intravaginal, nasal, topical or parenteral administration (including intravenous, intracavernosal, intramuscular, subcutaneous, and intratubular administration). For example, the compound according to the present invention may be orally or sublingually administered in a tablet form containing starch or lactose, a capsule form containing only the compound according to the present invention or containing an excipient in addition to the compound, or an elixir or suspension form containing a chemical for flavor or color. A liquid formulation is prepared together with a pharmaceutically acceptable additive such as a suspending agent (for example, methylcellulose, semisynthetic glycerides such as Witepsol, glyceride mixture such as a mixture of apricot kernel oil and polyethylene glycol (PEG)-6 ester or a mixture of PEG-8 and caprylic/capric glyceride). Further, in the case in which the pharmaceutical composition is parenterally, for example, intravenously, intracavernosally, intramuscularly, subcutaneously, and intratubularly injected, it is most preferable that the pharmaceutical composition is used in a sterile aqueous solution form. In this case, the solution may contain other materials (for examples, salts or polysaccharides such as mannitol or glucose) so as to be isotonic with blood.

More specifically, the pharmaceutical composition according to an exemplary embodiment of the present invention may be used in a form of tablets, pills, capsules, granules, powders, solutions, patches, transdermal absorption patches using a microneedle, or injections.

The ceramide derivative represented by Chemical Formula 1 according to the present invention may be used in a form of the pharmaceutically acceptable salt, and as the salt, an acid addition salt formed by a pharmaceutically acceptable free acid may be used. The acid addition salt is obtained from inorganic acids such as hydrochloric acid, nitric acid, phosphoric acid, sulfuric acid, hydrobromic acid, hydroiodic acid, nitrous acid, or phosphorous acid, non-toxic organic acids such as aliphatic mono- and di-carboxylate, phenyl-substituted alkanoates, hydroxy alkanoates, and alkanedioates, aromatic acids, aliphatic and aromatic sulfonic acids, and organic acids such as acetic acid, benzoic acid, citric acid, lactic acid, maleic acid, gluconic acid, methanesulfonic acid, 4-toluenesulfonic acid, tartaric acid, fumaric acid. Examples of these pharmaceutically non-toxic salts may include sulfate, pyrosulfate, bisulfate, sulfite, bisulfite, nitrate, phosphate, mono-hydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dionate, hexane-1,6-dionate, benzoate, chlorobenzoate, methylbenzoate, dinitro benzoate, hydroxybenzoate, methoxybenzoate, phthalate, terephthalate, benzene sulfonate, toluene sulfonate, chlorobenzene sulfonate, xylene sulfonate, phenylacetate, phenyl propionate, phenyl butyrate, citrate, lactate, β-hydroxybutyrate, glycolate, malate, tartrate, methanesulfonate, propanesulfonate, naphthalene-1-sulfonate, naphthalene-2-sulfonate or mandelate, but are not limited thereto.

Since the ceramide derivative represented by Chemical Formula 1 has an agonistic activity against a cannabinoid receptor 1 (CB1R), the pharmaceutical composition according to an exemplary embodiment of the present invention is useful to treat diseases regulated by a cannabinoid receptor activation.

In addition, the present invention provides a cosmetic composition for alleviating a skin disease, containing a novel ceramide derivative represented by Chemical Formula 1, or a pharmaceutically acceptable salt or solvate thereof as an active ingredient.

In the cosmetic composition for alleviating a skin disease according to an exemplary embodiment of the present invention, the skin disease may be one or more selected from the group consisting of atopic dermatitis, allergic rhinitis, psoriasis, contact dermatitis, eczematous dermatitis, photodermatitis, seborrheic dermatitis, dermatitis herpetiformis, lichen planus, lichen sclerosus, pyoderma gangrenosum, pemphigus, epidermolysis bullosa, angioedema, blepharitis, allergic conjunctivitis, degenerative or inflammatory ophthalmitis, arthritis, rheumatoid arthritis, spondylitis, systemic sclerosis, dermatomyositis, polymyositis, inflammatory muscle diseases, acquired immune deficiency syndrome (AIDS), leprosy, Sezary syndrome, inflammatory bowel diseases, stress diseases, and transplant rejection.

Hereinafter, preferred Examples of the present invention will be provided in order to assist in understanding of the present invention. However, the following Examples are provided only for easily understanding the present invention as illustrative examples, but the scope of the present invention is not limited thereto.

EXAMPLE 1

Preparation of (11Z)-2-((Z)-hexadec-7-enyl)-N-(1,3-dihydroxypropan-2-yl)-3-oxoicos-11-enamide (CBS007)

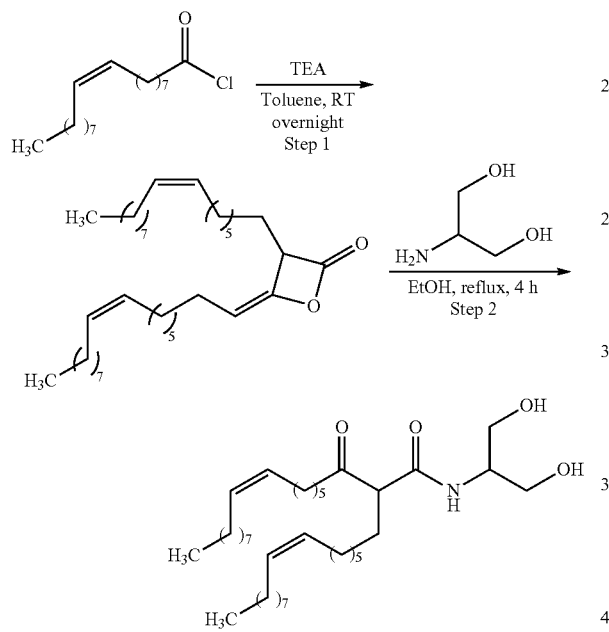

Preparation of (4E)-4-((Z)-heptadec-8-enylidene)-3-((Z)-hexadec-7-enyl)oxetan-2-one 30 ml of toluene was put into a 100 ml reactor under nitrogen atmosphere and 2.3 ml of TEA (16.62 mmol) was added thereto. After a temperature of the reactor was cooled to 0° C. or less using an ice bath, 5.5 ml of Octanoyl chloride (16.62 mmol) was slowly added thereto dropwise. After dropwise addition was completed, the ice bath was removed, and the temperature of the reactor was slowly raised to room temperature, followed by stirring overnight. Purified water was added to the reactant, c-HCl was added thereto to adjust a pH to 3, and purified water and ethyl acetate were additionally added thereto, stirred, and allowed to stand, thereby separating an organic layer. After the organic layer was washed with brine once, dried over $MgSO_4$, and filtered, the filtrate was concentrated under reduced pressure. The residue was separated using column chromatography (ethyl acetate:hexane=1:40), thereby obtaining (4E)-4-((Z)-heptadec-8-enylidene)-3-((Z)-hexadec-7-enyl)oxetan-2-one, which is an oleoylketenedimer, as a pale yellow liquid.

EXAMPLE 1

Preparation of (11Z)-2-((Z)-hexadec-7-enyl)-N-(1,3-dihydroxypropan-2-yl)-3-oxoicos-11-enamide (CBS007)

1.3 g of (4E)-4-((Z)-heptadec-8-enylidene)-3-((Z)-hexadec-7-enyl)oxetan-2-one (2.46 mmol) was dissolved in 13 ml of ethanol and 448 mg of serinol (4.92 mmol) was added thereto, followed by refluxing and stirring for 4 hours. A reaction was checked using thin layer chromatography (TLC), and the solvent was removed by concentration under reduced pressure. The ethylacetate and purified water were added to the concentrate and c-HCl was added thereto to adjust a pH to 3, followed by stirring and being allowed to stand, thereby separating an organic layer. The organic layer was dried over MgSO4, and a filtered filtrate was concentrated under reduced pressure, thereby completely removing the solvent. The residue was separated using column chromatography (dichloromethane:methanol=40:1), thereby obtaining a title compound (11Z)-2-((Z)-hexadec-7-enyl)-N-(1,3-dihydroxypropan-2-yl)-3-oxoicos-11-enamide (CBS007) (1.1 g, 1.77 mmol, 72% yield) as a pale yellow sticky liquid.

MS (ESI pos. ion) m/z: 621 (MH+). Calc.d exact mass for C39H73NO4: 620. $^1$H NMR (600 MHz, $CDCl_3$): 6.87 (d, J=7.2 Hz, 1H), 5.38-5.30 (m, 4H), 3.95-3.91 (m, 1H), 5.85-3.82 (m, 2H), 3.80-5.75 (m, 2H), 3.40 (t, J=7.2 Hz, 1H), 2.58-2.50 (m, 2H), 2.04-1.95 (m, 8H), 1.85-1.80 (m, 2H), 1.64-1.54 (m, 4H), 1.30-1.20 (m, 40H), 0.88 (t, J=7.2 Hz, 6H).

EXAMPLE 2

Preparation of (11Z)-2-((Z)-hexadec-7-enyl)-N-(2-hydroxyethyl)-3-oxoicos-11-enamide (CBS004)

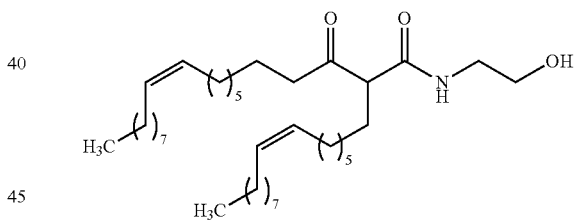

A title compound, (11Z)-2-((Z)-hexadec-7-enyl)-N-(2-hydroxyethyl)-3-oxoicos-11-enamide (CBS004) was obtained by a method similar to that in Example 1.

MS (ESI pos. ion) m/z: 590 (MH+). Calc.d exact mass for C38H71NO3: 589.98. $^1$H NMR (600 MHz, $CDCl_3$): 6.76 (t, J=5.4 Hz, 1H), 5.37-5.31 (m, 4H), 3.71 (t, J=5.4 Hz, 2H), 3.43-3.40 (m, 3H), 2.56-2.52 (m, 2H), 2.02-1.98 (m, 9H), 1.83-1.78 (m, 2H), 1.65-1.62 (m, 3H), 1.58-1.54 (m, 2H), 1.32-1.22 (m, 37H), 0.88 (t, J=7.2 Hz, 6H).

EXAMPLE 3 cAMP Production Suppression by Cannabinoid Receptor Agonist According to the Present Invention cAMP production suppression efficacy by agonistic action of the synthesized materials was confirmed using CHO cells in which cannabinoid receptor 1 (CB1R) was over-expressed.

The CHO cells in which the cannabinoid receptor 1 (CB1R) was over-expressed were purchased from Chantest, and cultured in an F-12 medium (Gibco) containing 10% fetal bovine serum (FBS, Gibco). In order to conform an agonistic activity of a ceramide derivative compounds according to the present invention on the cannabinoid receptor, the cells were plated in a 96-well dish, cultured for 24 hours, and then, treated at concentrations of 0, 0.781, 1.562, 3.125, 6.25, 12.5, 25, and 50 µM (0.1% DMSO in PBS). The cells were treated with 10 µM Forskolin (Sigma), thereby inducing cAMP production by adenylyl cyclase in the cells. A concentration of cAMP in the cells was measured using a HTRF cAMP assay kit purchased from Cisbio. After dissolving the cells with lysis buffer in the kit according to the manufacturer's manual, anti-cAMP cryptate conjugate and cAMP-d2 in the kit were treated at room temperature for 2 hours. Thereafter, fluorescence was measured at 665 nm and 620 nm and compensated by a ratio of 665 nm/620 nm, and then, the concentration of cAMP in the cells was measured using a standard curve. Since activity of adenylyl cyclase was suppressed when the cannabinoid receptor 1 (CB1R) was activated, the cannabinoid receptor agonist according to the present invention suppresses production of cAMP in the cells. As illustrated in FIG. 1, it may be confirmed that when the cells were treated with the compounds (CBS004 and CBS007) according to the present invention, the concentration of cAMP was decreased dependently on the concentration of the compound. As illustrated in the following Table 1, it may be confirmed that the novel cannabinoid receptor agonists according to the present invention activate the cannabinoid receptor 1 (CB1R) when EC50 was 24 to 26 µM.

TABLE 1

| Compounds | EC50 (µM) | Target | Activity | Modulation |
| --- | --- | --- | --- | --- |
| CBS004 | 24.2 | CB1R | +++ | Agonist |
| CBS007 | 26.7 | CB1R | ++ | Agonist |

EXAMPLE 4

Figure 2:
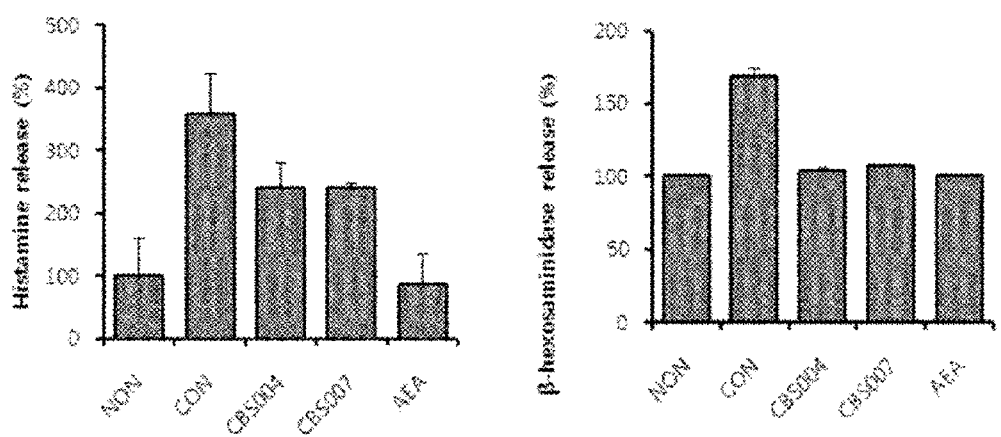

Suppression Effect by Cannabinoid Receptor Agonist According to the Present Invention in Mast Cells Activated by Ionomycin In order to confirm whether or not the ceramide derivative compound according to the present invention suppresses activation of the mast cells, RBL-2H3 cells (rat basophilic leukemia cells) corresponding to one kind of mast cells were cultured in a DMEM medium containing 10% FBS in a 24-well plate, and then treated with the compound for 16 hours. In order to induce degranulation of the mast cells, the cells were treated with 2 µM ionomycin (Sigma), and after 30 minutes, concentrations of β-hexosaminidase and histamine released to the medium were measured. In detail, at the time of measuring the concentration of β-hexosaminidase, 50 µl of the medium was reacted together with 50 µl of p-nitrophenyl-nacetyl-β-d-glucosaminidine, (p-NAG, Sigma) at 37° C. for 2 hours, and then, the reaction was terminated by adding 200 µl of 0.2 M glycine (pH 10.6, Sigma). Absorbance at a wavelength of 405 nm was measured using a spectrometer. The concentration of histamine was measured using a HTRF histamine assay kit (Cisbio). 10 µl of a medium supernatant of the cells was treated with anti-histamine cryptate conjugate and histamine-d2 according to the manufacturer's manual at room temperature for 2 hours. Thereafter, fluorescence was measured at 665 nm and 620 nm and compensated by a ratio of 665 nm/620 nm, and then, the concentration of histamine in the cells was measured using a standard curve. As illustrated in FIG. 2, it was confirmed that when the mast cells were treated with the cannabinoid receptor agonists according to the present invention, release of β-hexosaminidase and histamine was suppressed in the mast cells activated by ionomycin. Anandamide (AEA), which is a CB1R agonist, was used as a positive control.

EXAMPLE 5

Figure 3:
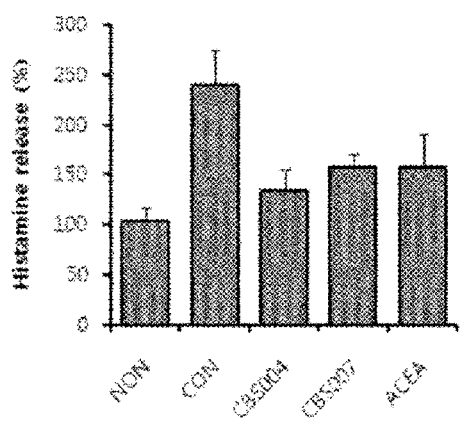
Figure 3:
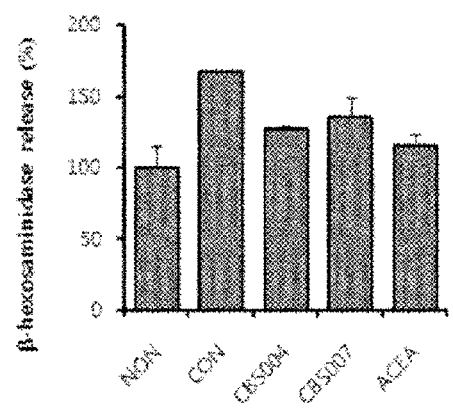

Suppression Effect by Cannabinoid Receptor Agonist According to the Present Invention in Mast Cells Activated by IgE Antibody and Antigen In order to confirm whether or not the ceramide derivative compound according to the present invention suppresses activities of the mast cells, RBL-2H3 cells (rat basophilic leukemia cells) corresponding to one kind of mast cells were cultured in a DMEM medium containing 10% FBS in a 24-well plate, and then treated with the compound for 16 hours. In order to induce degranulation of the mast cells, the cells were treated with IgE antibody (0.2 µg/ml) and NP-BSA (0.1 µg/ml) for 1 hour, and then, concentrations of β-hexosaminidase and histamine released to the medium were measured. In detail, at the time of measuring the concentration of β-hexosaminidase, 50 µl of the medium was reacted together with 50 µl of p-nitrophenyl-nacetyl-β-d-glucosaminidine, (p-NAG, Sigma) at 37° C. for 2 hours, and then, the reaction was terminated by adding 200 µl of 0.2 M glycine (pH 10.6, Sigma). Absorbance at a wavelength of 405 nm was measured using a spectrometer. The concentration of histamine was measured using a HTRF histamine assay kit (Cisbio). 10 µl of a medium supernatant of the cells was treated with anti-histamine cryptate conjugate and histamine-d2 according to the manufacturer's manual at room temperature for 2 hours. Thereafter, fluorescence was measured at 665 nm and 620 nm and compensated by a ratio of 665 nm/620 nm, and then, the concentration of histamine in the cells was measured using a standard curve. As illustrated in FIG. 3, it was confirmed that when the mast cells were treated with the cannabinoid receptor agonists according to the present invention, release of (β-hexosaminidase and histamine was suppressed in the mast cells activated by the IgE antibody. The suppression effect as described above was similar to or more excellent than that of ACEA, which is a well-known CB1R agonist.

EXAMPLE 6

Suppression Effect by Cannabinoid Receptor Agonist According to the Present Invention in Mast Cells Activated by Protease Activated Receptor-2 (PAR-2)

Figure 4:
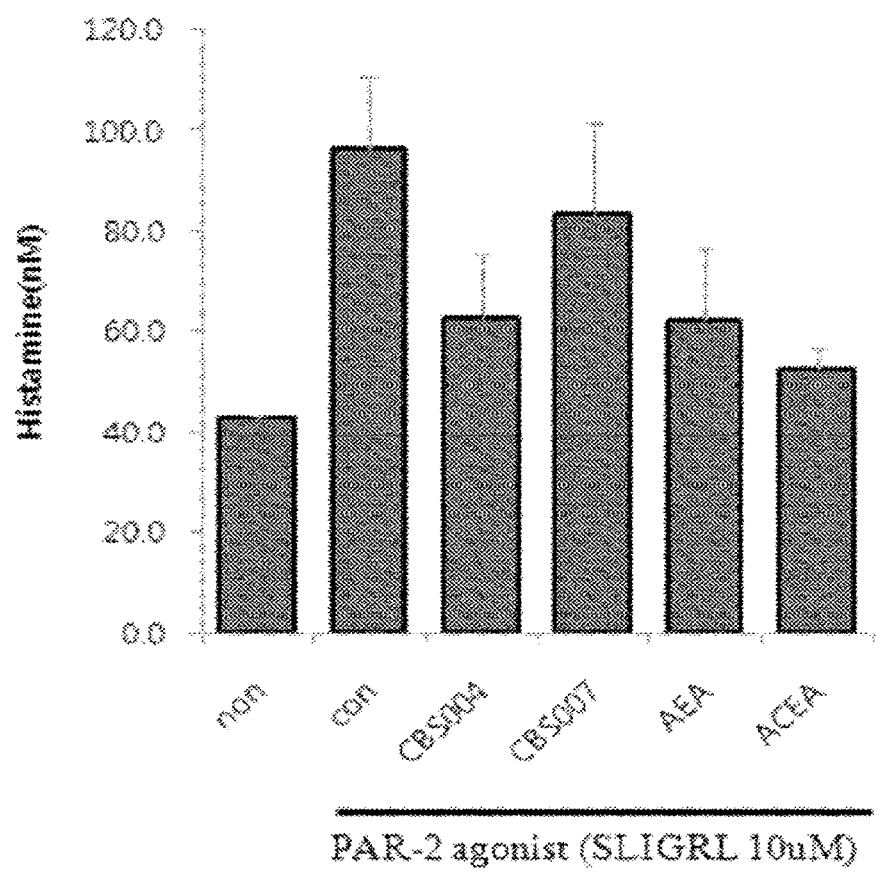
FIG. 4 is a graph illustrating suppression effects of the compounds CBS004 (Example 2) and CBS007 (Example 1) according to the present invention on activation of mast cells by protease activated receptor 2 (PAR-2) in Example 6.

The PAR-2, which is a receptor activated by protease (tryptase, chymase, and the like) present outside cells, induces degranulation on surfaces of the mast cells. In order to confirm whether or not the ceramide derivative compound according to the present invention suppresses activities of the mast cells by PAR-2, RBL-2H3 cells (rat basophilic leukemia cells) corresponding to one kind of mast cells were cultured in a DMEM medium containing 10% FBS in a 24-well plate, and then treated with the compound for 2 hours. Thereafter, in order to induce degranulation of the mast cells, the cells were treated with 10 μM SLIGRL peptide, which is a PAR-2 agonist, for 1 hour. The concentration of histamine released outside the cells was measured using a HTRF histamine assay kit (Cisbio). 10 μl of a medium supernatant of the cells was treated with anti-histamine cryptate conjugate and histamine-d2 according to the manufacturer's manual at room temperature for 2 hours. Thereafter, fluorescence was measured at 665 nm and 620 nm and compensated by a ratio of 665 nm/620 nm, and then, the concentration of histamine in the cells was measured using a standard curve. As illustrated in FIG. 4, it was confirmed that when the mast cells were treated with the cannabinoid receptor agonist according to the present invention, release of histamine in the mast cells activated by the PAR-2 agonist was suppressed. Therefore, the novel ceramide derivative according to the present invention, which is the novel cannabinoid receptor agonist, is a compound effectively suppressing the activities of the mast cells.

EXAMPLE 7

Figure 5:
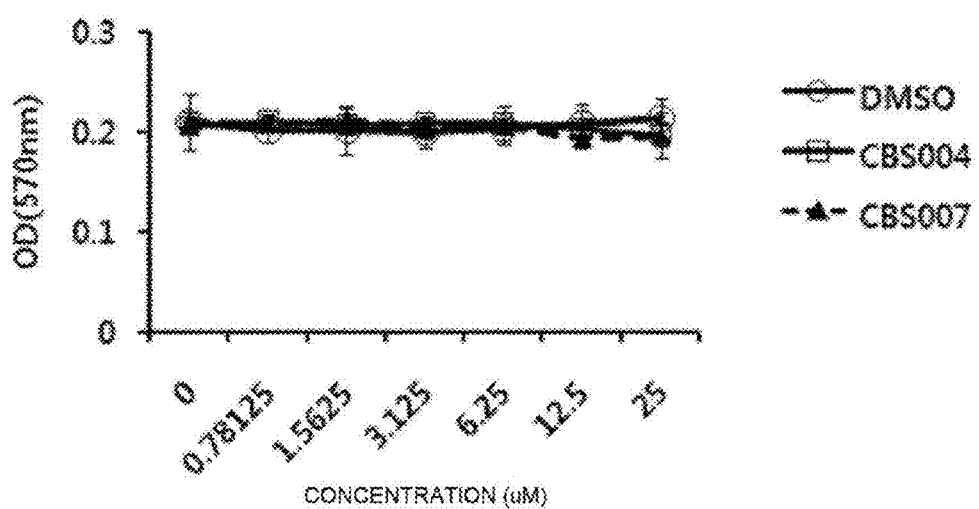
FIG. 5 is a graph illustrating cytotoxicity of the compounds CBS004 (Example 2) and CBS007 (Example 1) according to the present invention at each concentration in Example 7.

Evaluation of Cytotoxicity of Novel Cannabinoid Receptor Agonist According to the Present Invention In order to evaluate cytotoxicity of the ceramide derivative compound according to the present invention, on day 1, $5 \times 10^3$ of RBL-2H3 mast cells were cultured in a DMEM medium containing 10% fetal bovine serum (FBS) in each well of a 96-well plate. After 24 hours, cells were treated with cannabinoid receptor agonists at each concentration and cultured in an incubator (37° C., 5% $CO_2$) for 12 hours. In order to confirm living cells, 10 μl of 3-4,5-dimethylthhenyliazol-2-yl)-2,5-diphenyltetrazolium bromide (MTT, Sigma) was added to the medium. After culturing the cells at 37° C. for 4 hours, the medium was removed. Then, after confirming that a color was purple when 100 μl of dimethyl sulfoxide (DMSO) was added thereto, absorbance was measured at a wavelength of 570 nm using a spectrometer. As illustrated in FIG. 5, since the number of living cells was not decreased even though the concentration of the synthesized material treated in the RBL-2H3 mast cells was increased, it may be appreciated that the ceramide derivative compound according to the present invention does not have toxicity to the mast cells, and when the ceramide compound derivative is used in human, the ceramide derivative compound is non-toxic.

EXAMPLE 8

Figure 6:
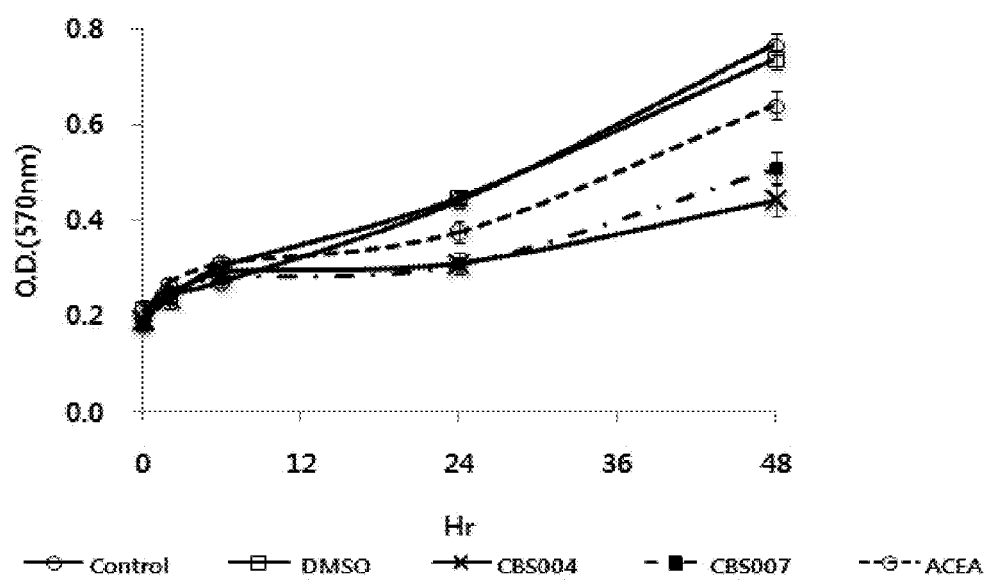
FIG. 6 is a graph illustrating influences of the compounds CBS004 (Example 2) and CBS007 (Example 1) according to the present invention on proliferation of mast cells in Example 8, FIG. 7(A) and (B) are photos and a graph illustrating repair effects of the compounds CBS004 (Example 2) and CBS007 (Example 1) according to the present invention on skin damage in an atopic dermatitis-induced animal model in Example 9, FIG. 8(A) and (B) are a graphs illustrating decrease effects of the compounds CBS004 (Example 2) and CBS007 (Example 1) according to the present invention on concentrations of histamine (B) and IgE antibody (A) in the blood in an atopic dermatitis-induced animal model in Example 10.

Suppression Efficacy of Novel Cannabinoid Receptor Agonist According to the Present Invention on Cell Proliferation In order to confirm an influence of the ceramide compound derivative according to the present invention on cell proliferation, $5 \times 10^3$ of RBL-2H3 mast cells were cultured in a DMEM medium containing 10% fetal bovine serum (FBS) in each well of a 96-well plate. After 24 hours, cells were treated with cannabinoid agonists (concentration: 25 μM) and cultured in an incubator (37° C., 5% $CO_2$) for 48 hours. In order to confirm living cells, the number of cells was confirmed after 0, 2, 6, 24, and 48 hours by using 3-4,5-dimethylthhenyliazol-2-yl)-2,5-diphenyltetrazolium bromide (MTT, Sigma) assay. In more detail, 10 μl of MTT was added to the medium, the cells were cultured at 37° C. for 4 hours. After removing the medium and confirming that a color was purple when 100 μl of dimethyl sulfoxide (DMSO) was added thereto, absorbance was measured at a wavelength of 570 nm using a spectrometer. As illustrated in FIG. 6, it may be appreciated that after the RBL-2H3 cells were treated with the ceramide derivative compound according to the present invention, the number of cells was decreased as compared to a case in which the RBL-2H3 cells were not treated with the ceramide derivative compound. Therefore, it may be concluded that the ceramide compound derivative according to the present invention may serve as a cannabinoid receptor agonist to suppress proliferation of the mast cells, thereby further decreasing the number of cells over time.

EXAMPLE 9

Figure 7:
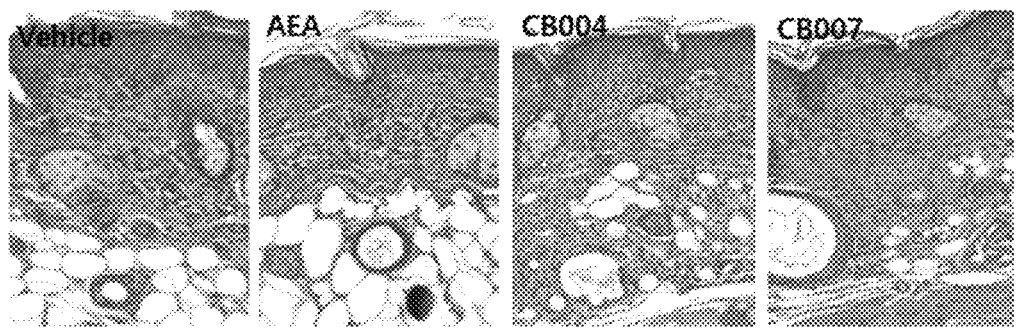
Figure 7:
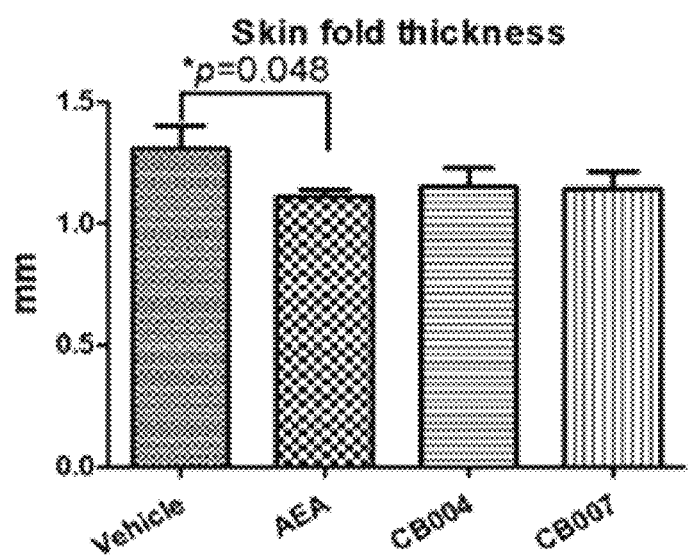

Suppression Function of Novel Compound According to the Present Invention in Oxazolone-Induced Atopic Dermatitis Animal Model In order to evaluate efficacy of the novel compound according to the present invention in an animal model, first, hairless mice were treated with oxazolone (Sigma), thereby establishing atopic dermatitis-like animal models. More specifically, on day 1, the mice were sensitized with 1% oxazolone in acetone on the back, and after 1 week, the mice were treated with 0.1% oxazolone in acetone on the back every other day for 2 weeks, thereby inducing atopic dermatitis-like symptoms. Thereafter, the compound (1%) according to the present invention was dissolved in a solution in which polyethylene glycol (PEG, Sigma) and ethanol were mixed with each other at a ratio of 7:3, and the mice were treated with the obtained compound solution on the back once in the morning and evening for 10 days. As illustrated in FIG. 7, it may be appreciated that in the skin treated only with a vehicle, atopic dermatitis was induced, such that the skin became significantly thick as compared to the normal skin, but in a compound-treated group, the skin thickness maintained similar to that of normal mice. In addition, a skin thickness of each of the animal models was measured and illustrated by a graph. When the atopic dermatitis model animal was treated with the compound according to the present invention, atopic dermatitis-like symptoms were significantly alleviated. Therefore, the compound according to the present invention may be effective to treat atopic dermatitis.

EXAMPLE 10

Figure 8:
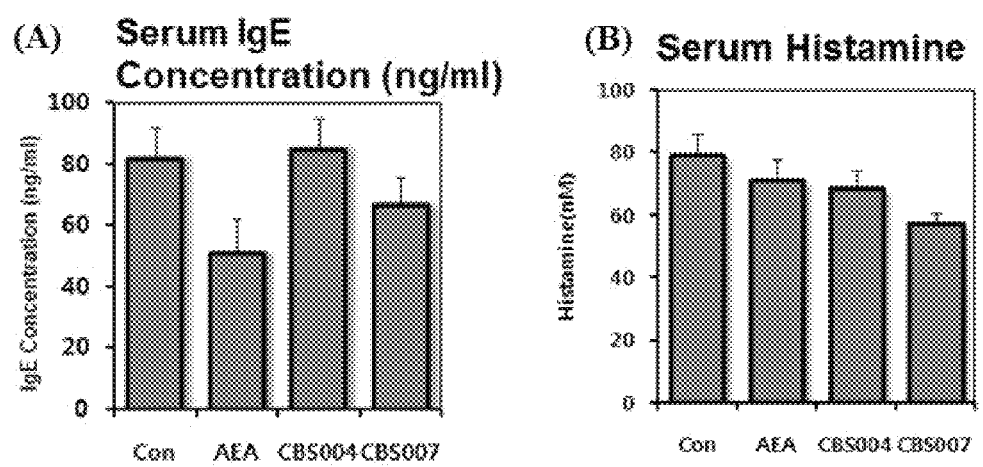

Alleviating Effect of Novel Compound According to the Present Invention on IgE and Histamine in Blood in Atopic Dermatitis Animal Model In order to evaluate efficacy of the novel compound according to the present invention in an atopic dermatitis animal model, after treating an oxazolone (Sigma)-induced atopic dermatitis animal model with the compound, concentrations of IgE antibody and histamine present in the blood were measured. The IgE and histamine in the blood are known as markers of atopic dermatitis and inflammatory dermatitis such as contact dermatitis, and as the disease aggregates, the concentrations thereof in the blood further increases. The increased IgE activated mast cells, and allowed the mast cells to release a large amount of inflammatory cytokines such as histamine. As illustrated in FIG. 8, it may be appreciated that when the atopic dermatitis animal model was treated with the compound according to the present invention, the concentrations of IgE and histamine in the blood were decreased. The result as described above indicates that the compound according to the present invention is effective to treat atopic dermatitis.

EXAMPLE 11

Figure 9:
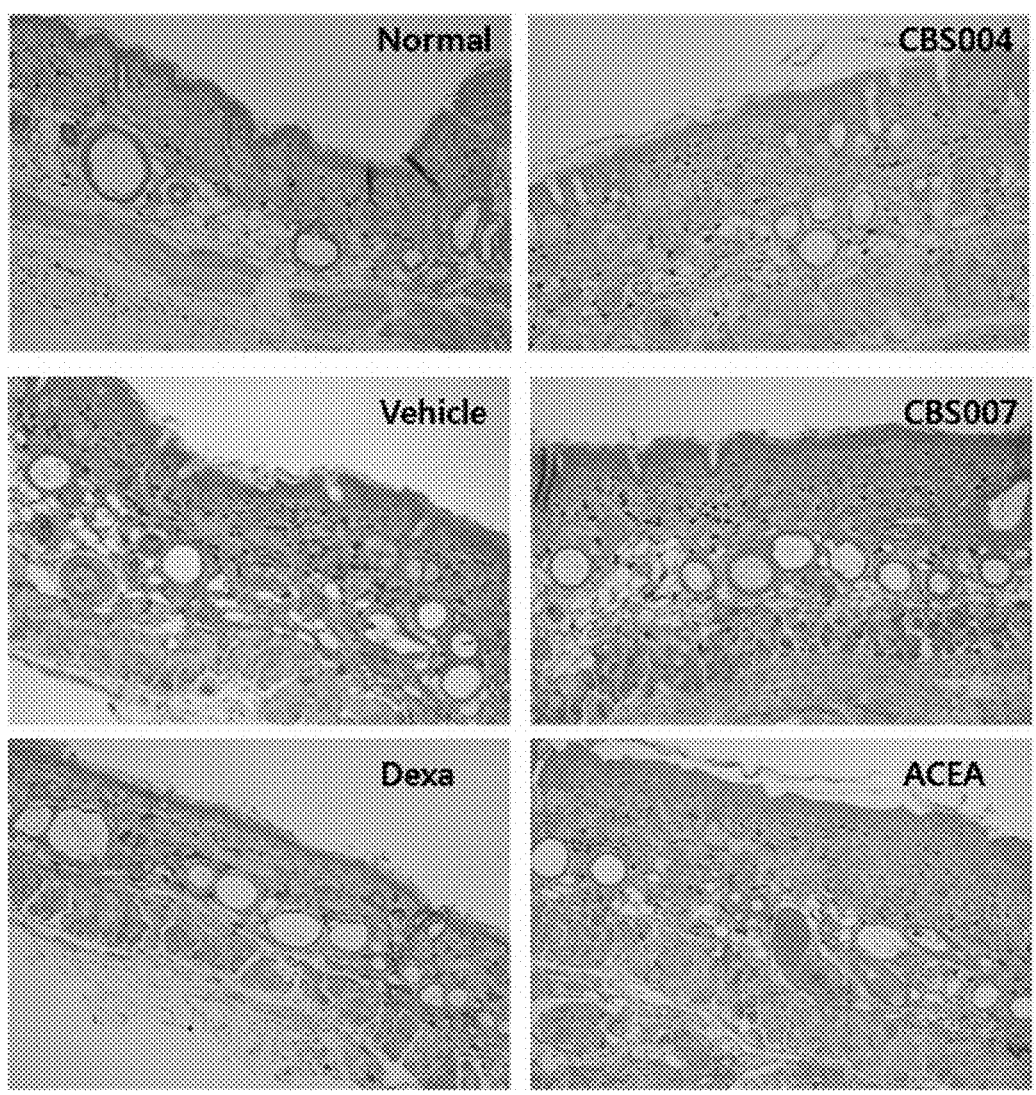
FIG. 9 is a view illustrating that invasion of mast cells is suppressed in a lesion site in an atopic dermatitis-induced animal model by a method according to Example 11, using the compounds CBS004 (Example 2) and CBS007 (Example 1) according to the present invention.
Figure 10:
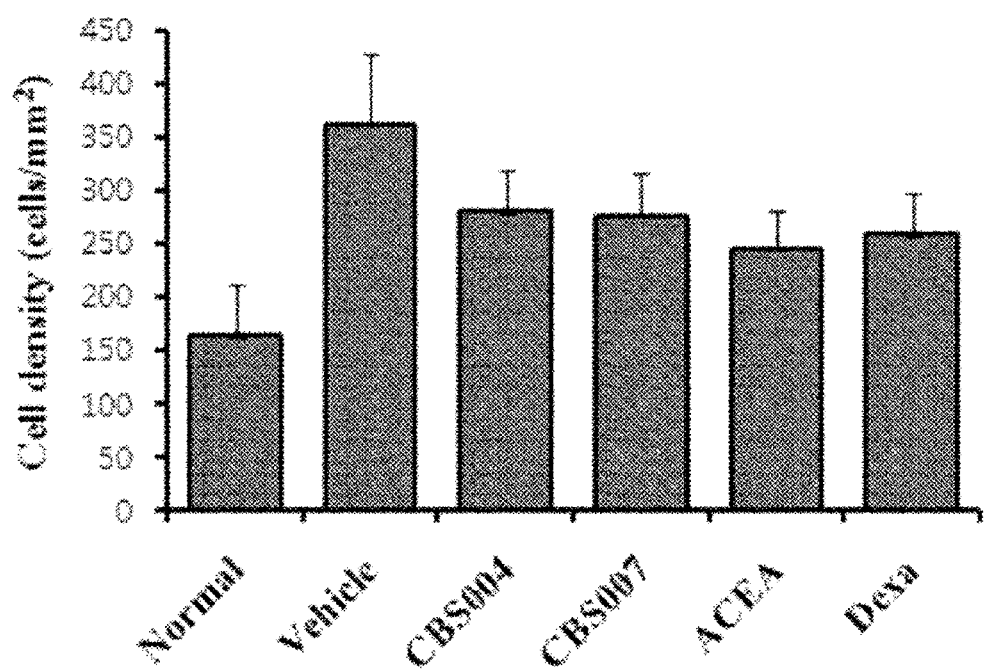
FIG. 10 is a graph illustrating that the number of mast cells present in the skin of an atopic dermatitis-induced animal model by the method according to Example 11, using the compounds CBS004 (Example 2) and CBS007 (Example 1) according to the present invention.

Suppression Effects of Novel Compound According to the Present Invention on Activities of Mast Cells in Atopic Dermatitis Animal Model In order to evaluate whether or not the novel compound according to the present invention suppresses the activities of mast cells in an atopic dermatitis animal model, first, hairless mice were treated with oxazolone (Sigma), thereby establishing an atopic dermatitis animal model. More specifically, on day 1, mice were sensitized with 1% oxazolone in acetone on the back, and after 1 week, the mice were treated with 0.1% oxazolone in acetone on the back every other day for 2 weeks, thereby inducing atopic dermatitis on the back skin of the mice. Thereafter, the compound (1%) according to the present invention was dissolved in a solution in which polyethylene glycol (PEG, Sigma) and ethanol were mixed with each other at a ratio of 7:3, and the mice were treated with the obtained compound solution on the back once in the morning and evening for 10 days. Then, skin biopsy was taken and stained with toluidine blue solution (Sigma), thereby confirming presence of mast cells. As illustrated in FIG. 9, in the normal skin, a small amount of mast cells were observed, but after atopic dermatitis-like symptom was induced, a large amount of mast cells were observed, as illustrated in a group treated only with a vehicle. The mast cells in the skin as described above release various kinds of inflammatory cytokines, thereby aggregating atopic dermatitis. On the contrary, it may be confirmed that on the skins of the mice treated with the compound according to the present invention, the number of mast cells was significantly decreased. The number of mast cells present on the skin in each of the groups was statistically analyzed and illustrated by a graph. As illustrated in FIG. 10, when the atopic dermatitis-like animal model was treated with the compound according to the present invention, the number of mast cells in the skin of the lesion site was decreased by about 30%. Therefore, when an atopic dermatitis patient is treated with the compound according to the present invention, the compound may suppress activities and proliferation of mast cells, such that the compound may be effective to treat atopic dermatitis.

INDUSTRIAL APPLICABILITY

A novel ceramide derivative and a pharmaceutically acceptable salt or solvate thereof according to the present invention, which are excellent cannabinoid receptor agonists, may be synthesized using a simple synthesis process as compared to a cannabinoid receptor agonist according to the related art, and decrease a process time and a cost of a raw material, thereby having advantages of economical efficiency and ease of emulsification at the time of being formulated into a cosmetics or medicine.

In addition, the novel ceramide derivative and the pharmaceutically acceptable salt or solvate thereof according to the present invention may act as a cannabinoid receptor agonist to suppress activities of mast cells, thereby being usefully used to treat and prevent a skin disease.

Further, a cosmetic composition according to the present invention may contain a novel ceramide derivative, or a pharmaceutically acceptable salt or solvate thereof having an excellent agonistic effect on a cannabinoid receptor as an active ingredient, thereby making it possible to prevent and treat a skin disease.

The invention claimed is:

1. A pseudoceramide compound of the following chemical formula (1), or a pharmaceutically acceptable salt thereof:

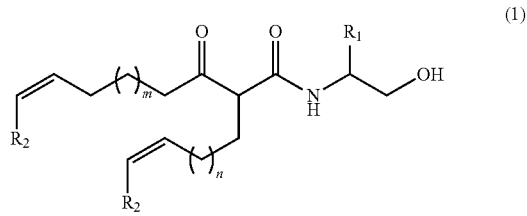

wherein $R_1$ is hydrogen or a hydroxy(C1-C10)alkyl, $R_2$ is a (C1-C10)alkyl, and m and n are integers of 1 to 10.

2. The pseudoceramide compound of claim 1 or the solvates thereof, which is selected from the following compounds:

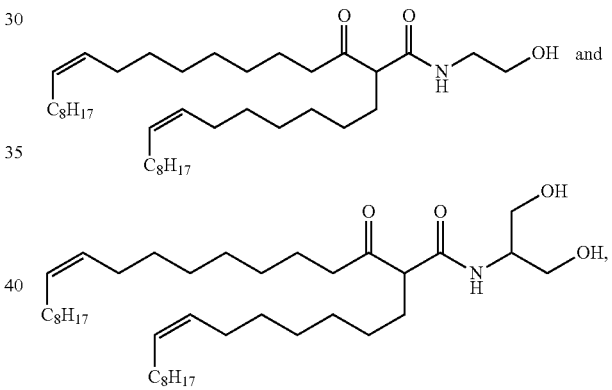

or a pharmaceutically acceptable salt thereof.

3. A pharmaceutical composition, comprising the pseudoceramide compound or the pharmaceutically acceptable salt thereof or the solvate thereof of claim 1 as an active ingredient and a pharmaceutically acceptable carrier.

4. A cosmetic composition, comprising the pseudoceramide compound or the pharmaceutically acceptable salt or the solvates thereof of claim 1 and a cosmetically acceptable carrier.

5. A pharmaceutical composition, comprising the pseudoceramide compound or the pharmaceutically acceptable salt thereof or the solvates thereof of claim 2 as an active ingredient and a pharmaceutically acceptable carrier.

6. A cosmetic composition, comprising the pseudoceramide compound or the pharmaceutically acceptable salt or the solvates thereof of claim 2 and a cosmetically acceptable carrier.

7. A method for treating a skin disease, comprising administering an effective amount of the pseudoceramide compound of claim 1 or a pharmaceutically acceptable salt thereof to a subject in need thereof, wherein the skin disease is selected from the group consisting of atopic dermatitis, psoriasis, contact dermatitis, eczematous dermatitis, photodermatitis, seborrheic dermatitis, dermatitis herpetiformis, lichen planus, lichen sclerosus, pyoderma gangrenosum, pemphigus, and epidermolysis bullosa.

8. A method for alleviating a skin disease, comprising applying an effective amount of the pseudoceramide compound of claim 1 or a pharmaceutically acceptable salt thereof to skin of a subject in need thereof, wherein the skin disease is selected from the group consisting of atopic dermatitis, psoriasis, contact dermatitis, eczematous dermatitis, photodermatitis, seborrheic dermatitis, dermatitis herpetiformis, lichen planus, lichen sclerosus, pyoderma gangrenosum, pemphigus, and epidermolysis bullosa.

9. A method for treating a skin disease, comprising administering an effective amount of the pseudoceramide compound or a pharmaceutically acceptable salt thereof of claim 2 to a subject in need thereof, wherein the skin disease is selected from the group consisting of atopic dermatitis, psoriasis, contact dermatitis, eczematous dermatitis, photodermatitis, seborrheic dermatitis, dermatitis herpetiformis, lichen planus, lichen sclerosus, pyoderma gangrenosum, pemphigus, and epidermolysis bullosa.

10. A method for alleviating a skin disease, comprising applying an effective amount of the pseudoceramide compound or a pharmaceutically acceptable salt thereof of claim 2 to skin of a subject in need thereof, wherein the skin disease is selected from the group consisting of atopic dermatitis, psoriasis, contact dermatitis, eczematous dermatitis, photodermatitis, seborrheic dermatitis, dermatitis herpetiformis, lichen planus, lichen sclerosus, pyoderma gangrenosum, pemphigus, and epidermolysis bullosa.

\* \* \* \* \*